United States Patent
Kroll

(10) Patent No.: US 7,596,412 B1
(45) Date of Patent: Sep. 29, 2009

(54) OPTO-ELECTRICAL COHERENCE DETECTION OF HEMODYNAMICALLY COMPROMISING ARRHYTHMIA

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 721 days.

(21) Appl. No.: 10/927,971

(22) Filed: Aug. 26, 2004

(51) Int. Cl.
*A61N 1/365* (2006.01)

(52) U.S. Cl. ...................................... 607/18

(58) Field of Classification Search .......... 607/18, 607/4–6
See application file for complete search history.

(56) References Cited

U.S. PATENT DOCUMENTS

| | | | | |
|---|---|---|---|---|
| 5,342,406 | A | | 8/1994 | Thompson ................ 607/22 |
| 5,431,172 | A | | 7/1995 | Hoegnelid et al. ........ 128/705 |
| 6,466,821 | B1 | * | 10/2002 | Pianca et al. ............. 607/18 |
| 7,076,300 | B1 | * | 7/2006 | Kroll et al. ............... 607/14 |
| 7,171,268 | B1 | * | 1/2007 | Kroll et al. ............... 607/5 |
| 7,212,861 | B1 | * | 5/2007 | Park et al. ................ 607/17 |
| 7,274,961 | B1 | * | 9/2007 | Kroll et al. ............... 607/4 |
| 7,286,875 | B1 | * | 10/2007 | Park et al. ................ 607/18 |
| 2004/0230129 | A1 | * | 11/2004 | Haefner .................... 600/510 |
| 2005/0288725 | A1 | * | 12/2005 | Hettrick et al. ........... 607/17 |

OTHER PUBLICATIONS

The coherence spectrum. A quantitative discriminator of fibrillatory and nonfibrillatory cardiac rhythms KM Ropella, AV Sahakian, JM Baerman and S Swiryn Circulation 1989;80;112-119.*

* cited by examiner

*Primary Examiner*—George R Evanisko

(57) ABSTRACT

System and methods for assessing sensed signals for determining a reliability measure of their accuracy with respect to a patient's true physiological status. As one example, the signals can include multiple, independently obtained signals, such as an electro-chemically based measure of cardiac activity and a plethysmography based measure of hemodynamic output which typically exhibit different morphologies and varying phase shifts with respect to each other. One manner of assessing the signals is to transform them into the frequency domain, such as via a Fast Fourier Transform (FFT), and evaluate them, such as by a coherence determination, to determine the degree of their mutual agreement. This can be used to assess the reliability of the sensing. Therapy can be delivered under certain observed conditions, such as a condition of hemodynamic insufficiency where anti-tachycardia pacing and/or shocking therapy can be delivered.

8 Claims, 5 Drawing Sheets

OPTO-ELECTRICAL COHERENCE DETECTION OF HEMODYNAMICALLY COMPROMISING ARRHYTHMIA

FIELD OF THE INVENTION

The invention relates to the field of implantable medical devices and, more particularly, to methods and system for evaluating sensors to determine a confidence measure of their output to improve delivery of therapy and accuracy of sensing patient conditions, such as hemodynamic insufficiency.

DESCRIPTION OF THE RELATED ART

Hemodynamic output refers to the volumetric output of blood pumped by the heart over time. Failure to pump an adequate volume of oxygenated blood at an adequate rate to support the patient's metabolic needs is referred to as hemodynamic compromise or hemodynamic insufficiency. Hemodynamic insufficiency can arise from a variety of causes including bradycardia involving an insufficient heart rate, insufficient cardiac output per cardiac cycle, such as arising from weakened cardiac tissue resulting in a lowered ejection volume and/or ejection fraction, as well as systemic obstructions or restrictions limiting blood flow.

A variety of sensors and methods of measurements are known to evaluate a patient's cardiac output, including the hemodynamic output. One example is pressure sensors that are provided to directly or indirectly monitor the pressure fluctuations throughout a cardiac cycle to provide an indicator of the patient's hemodynamic output. It is also known to use optically based sensors, such as reflectance or transmittance sensors, to perform a plethysmography measurement. One example of plethysmography is photoplethysmography which senses optical properties of a selected region of the patient's body to measure blood volume changes. Photoplethysmography (PPG) employs a photo emitter, such as an IR LED to direct light into the patient's tissue. This light either passes through the tissue in a transmittance type PPG sensor or is partially reflected in a reflectance time PPG sensor. The amount of light absorbed by the tissue or reflected by the tissue respectively is indicative of the blood content of the tissue. Thus, by proper placement and evaluation of a PPG sensor, relative changes in blood volume over time can be measured.

While these methods can provide a direct measurement indicative of the volumetric blood flow over time or hemodynamic output, they are subject to disruptive influences particularly when employed as sensors fixed to or implanted in a patient outside a clinical setting where there is often a greater likelihood of disruptions which can disturb their sensing so as to provide erroneous signals which degrades their reliability for providing a true indicator of the patient's instantaneous hemodynamic output. In particular, these sensors are measuring volumetric or pressure changes over time and thus are subject to mechanical disturbances which can cause variations in the volumetric or pressure measurements as sensed by the sensor but which may not have a true relation to the patient's actual hemodynamic output. For example, physical shocks which jar the patient or vigorous activity also generating mechanical shocks which can propagate through the patient's body cause pressure and volumetric fluctuations that do not truly correspond directly to the patient's hemodynamic output.

Accurately and reliably sensing a patient's true hemodynamic output is important in that occurrence of hemodynamic compromise or insufficiency would indicate prompt delivery of interventional therapy. However the aforementioned difficulties in employing a PPG sensor as a reliable indicator of hemodynamic output have limited the use of such sensors for diagnosis and initiation of therapy delivery, particularly with implantable medical devices in active patients outside a clinical setting.

The activity of the heart itself can also be examined as an indicator for hemodynamic output by examining the electrochemically based activity of the heart muscle, such as via an intracardiac electrogram (IEGM) and/or surface electrocardiogram (ECG) signal. These signals measure the electrical activity of the heart internally or at the skin surface respectively which provide measures of the cyclic depolarization and repolarization of the cardiac tissue. This gives an indication both of the strength of the cardiac contractions as well as their relative timing and rates. A particular concern is in a tachycardia condition where the IEGM and/or ECG signals indicate an elevated heart rate but which in certain circumstances, either through reduced pumping efficiency and/or lack of coordination among the chambers of the heart, an elevated heart rate can occur with a reduced hemodynamic output leading to hemodynamic insufficiency. A reliable measure of the actual hemodynamic output of the heart could be used as an indicator to induce an implantable stimulation device to apply therapy in case of an incidence of hemodynamic efficiency arising from a tachycardia condition, such as application of an anti-tachycardia pacing (ATP) regimen wherein the implantable device attempts to overdrive pace the heart so as to capture the intrinsic activity for a subsequent reversion to a reduced pacing rate or to intrinsic activity at an acceptable rate. However the aforementioned difficulties with direct measures of hemodynamic output, such as pressure and PPG sensors, have limited the effectiveness of such measures.

There are also difficulties with the reliability of other types of physiological parameter sensing, such as direct nerve sensing (e.g. phrenic or vagus nerve sensing) or sensing of cardiac activity in a noisy background. For example, muscle activity is accompanied by electrical signals commonly indicated by electromyograms (EMGs) and electromagnetic energy coupled to a person can present relatively large magnitude electrical signals internally at the sensing location that often encompass a similar frequency spectra as the physiological parameter of interest. Thus, there is a difficulty in reliably establishing a signal as corresponding to the physiological process and not noise. Another difficulty in the reliability of sensed signals is that, in certain applications, sensing with multiple sensors can encounter sensing time lags or phase shifts that can vary over time, thus complicating the evaluation of one signal in relation to another. Thus, while one or more sensors may be capable of providing more accurate and/or reliable data than others, a direct comparison to make this determination is frequently not readily feasible.

Thus, it will be appreciated that there is a need for a system and method for evaluating or establishing a reliability measure of sensed physiological activity to improve evaluation of the patient's true condition and for improved delivery of indicated therapy. One example is the aforementioned need for a reliable, direct measure of a patient's hemodynamic output. There is also a need for evaluating multiple independent sensors to provide indications of the relative reliability of the measurements made by the multiple sensors to allow selection of the sensor(s) providing the most reliable measurements to improve the efficacy of the condition evaluation and therapy delivery.

SUMMARY

In one embodiment, an implantable cardiac stimulation device is disclosed that comprises at least one lead adapted to be implanted in a patient so as to be able to deliver therapeutic stimulation to the heart of the patient, a first sensor adapted to be implanted in the patient so as to sense a first signal indicative of cardiac activity, a second sensor adapted to be implanted in the patient that senses a second physiological parameter of the patient to provide a second signal, and a controller that receives the signals from the first and second sensors, wherein the controller evaluates the signals to determine whether the second signal is frequency related to the first signal and, upon determining that the second signal is frequency related to the first signal, adjusts the delivery of the therapeutic stimulation to the heart of the patient based at least in part upon the second signal.

In a further embodiment, the controller transforms the first and second signals into a frequency domain and determines a correlation between the first and second signals in the frequency domain to ascertain whether the first and second signals have related frequency components. In a preferred embodiment, the controller transforms the signals into the frequency domain by decomposing the first and second signals from a time domain into a corresponding composition of sinusoids in the frequency domain and/or mathematically determines the correlation by calculating a coherence value defined as a scalar ratio of a cross-power spectrum of the two signals to the product of the auto-power spectra of each of the two signals.

In another preferred embodiment, the controller determines a correlation between the detected hemodynamic output and the patient's cardiac activity to determine whether sensed variations in the hemodynamic output correspond to variations in a volume of blood pumped by the heart or whether the sensed variations in the detected hemodynamic output are the result of factors unrelated to the volume of blood pumped by the heart. In this embodiment, upon determination that variations in the hemodynamic output do correspond to the patient's cardiac activity and that hemodynamic output is low, the device can implement an anti-tachycardia pacing therapy via the at least one lead.

An additional embodiment further comprises a third sensor adapted to be implanted in the patient that provides third signals indicative of a third physiological parameter of the patient, wherein the device correlates the second and third sensed signals and, if the second and third sensed signals do correlate, adjusts therapy delivery of the device based at least in part on the second signal. In one embodiment, upon a determination that correlation is lacking between the first and second and the second and third signals, the device determines a possible ventricular tachycardia condition and initiates application of a shocking therapy. Upon a determination that correlation is lacking between the first and second, but does exist between the second and third signals, the device can determine that the lack of correlation between the first and second signals is due to an elevated activity level and inhibit delivery of therapy for a period of time, absent other indicators.

Another embodiment is an implantable medical device comprising a controller, at least a first sensing and stimulation electrode providing first sensed signals having a first frequency spectrum to the controller, at least one physiological sensor providing second sensed signals having a second frequency spectrum to the controller, and a stimulation pulse generator receiving control signals from the controller so as to selectively provide stimulation signals to the at least one sensing and stimulation electrode wherein the device correlates the first and second sensed signals in a frequency domain and uses the determination of the correlation to determine a patient's physiological condition for delivery of therapeutic stimulation via the at least first sensing and stimulation electrode.

A further embodiment is an implantable medical device comprising a controller, at least one sensing electrode providing first sensed signals having a first frequency spectrum to the controller, at least two physiological sensors providing second and third sensed signals having second and third frequency spectra respectively to the controller, a stimulation pulse generator receiving control signals from the controller, and at least one stimulation electrode connected to the stimulation pulse generator so as to provide indicated stimulation therapy wherein the device correlates the first and the second and the second and the third sensed signals and, if correlation exists between the first and second signals, discounts a lack of correlation between the second and third sensed signals and delivers therapy based at least in part on the second signals and, if correlation exists between the second and third sensed signals, discounts a lack of correlation between the first and second sensed signals and delays delivery of therapy for a period of time absent other indicators for therapy delivery and, if correlation is lacking between both the first and the second and the second and the third sensed signals, initiates delivery of appropriate therapy.

Yet another embodiment is an implantable cardiac stimulation device comprising first means for sensing a first patient parameter, second means for sensing a second patient parameter, means for delivering stimulation therapy, and means for evaluating, the evaluating means being in communication with the first and second sensing means and the means for delivery of therapy, wherein the evaluating means receives signals sensed from the first and second sensing means, transforms the signals sensed from the first and second sensing means into a frequency domain, correlates the signals from the first sensing means with those of the second sensing means in the frequency domain, and induces delivery of therapy via the means for delivering stimulation therapy based at least in part on the correlation results and, if correlation is found between the signals from the first and second sensing means, upon the signals from the second sensing means.

An additional embodiment is a method of evaluating a patient condition and determining delivery of therapy comprising monitoring a first signal indicative of a first patient condition, monitoring a second signal indicative of a second patient condition, transforming the first and second signals into a frequency domain, evaluating the transformed signals in the frequency domain to determine a degree of correlation between the signals, and delivering therapy based at least in part upon the determination of the degree of correlation between the signals.

Thus, various embodiments provide the ability for an implantable device to self-monitor the signals provided by sensors monitoring patient physiological conditions to determine measures of the relative reliability of the signals being provided by the sensors. One embodiment employs an efficient transformation algorithm to transform the time based signals from multiple sensors into the frequency domain. This embodiment enables the device to readily note commonality in the frequency spectra of the multiple sensors and to accommodate phase shifts that are variable and problematic to evaluate in the time domain. This embodiment allows the device to perform the transformation and correlation within the constraints of the microcontroller and limited battery charge capacity of an implantable device. Certain embodiments also allow the device to accurately employ a relative sensitive sensor, such as a PPG sensor, to directly sense the volumetric and pressure fluctuations of the patient's blood flow to monitor and provide therapy for instances of hemodynamic insufficiency/compromise. These and other objects and advantages of the invention will be more apparent from the following description taken in conjunction with the accompanying drawings.

DETAILED DESCRIPTION OF THE PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
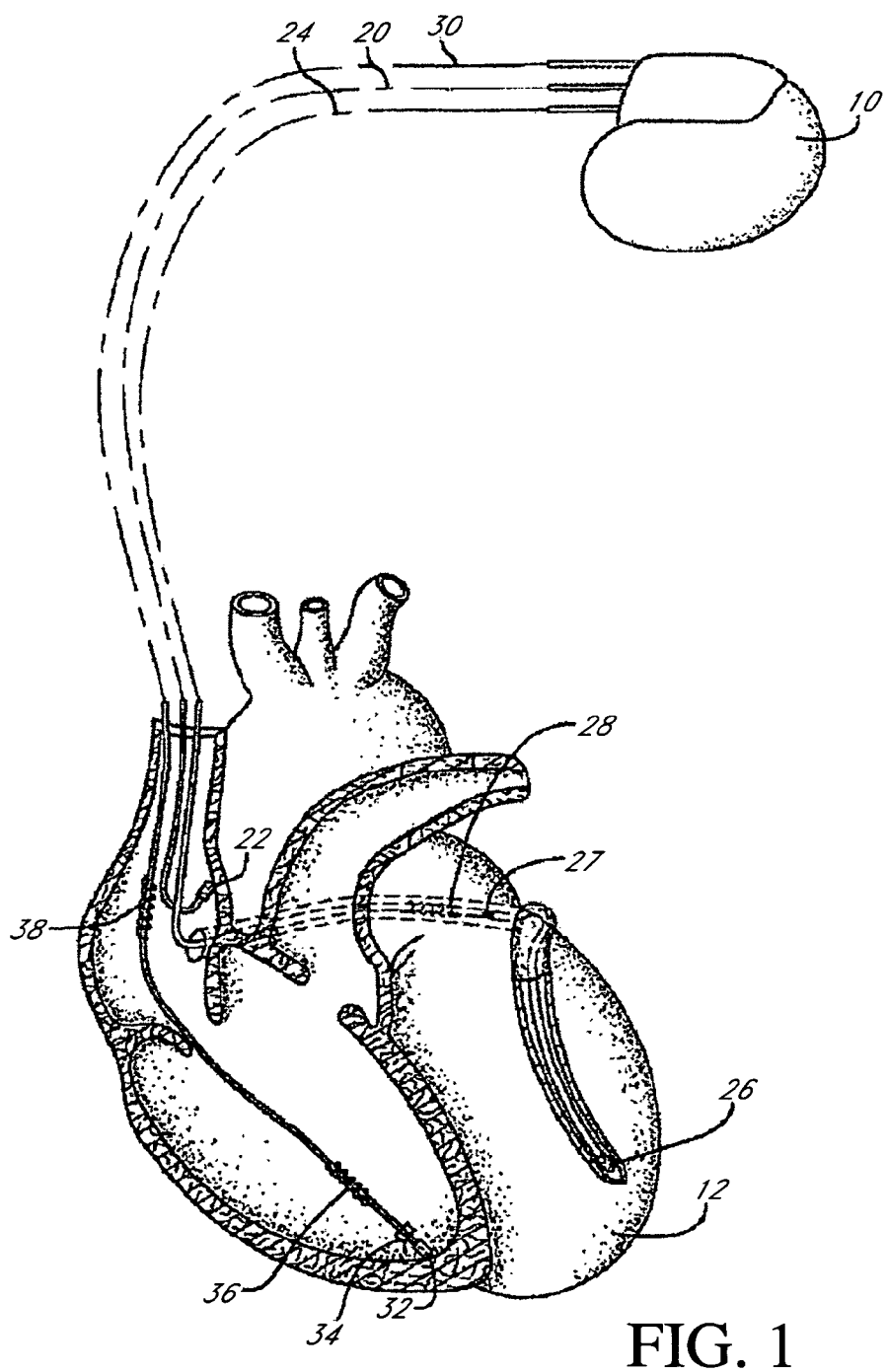
FIG. 1 is a simplified diagram illustrating an implantable stimulation device in electrical communication with at least three leads implanted into a patient's heart for delivering multi-chamber stimulation and shock therapy.

As shown in FIG. 1, there is an implantable stimulation device 10, referred to hereafter as "device 10" for brevity, in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
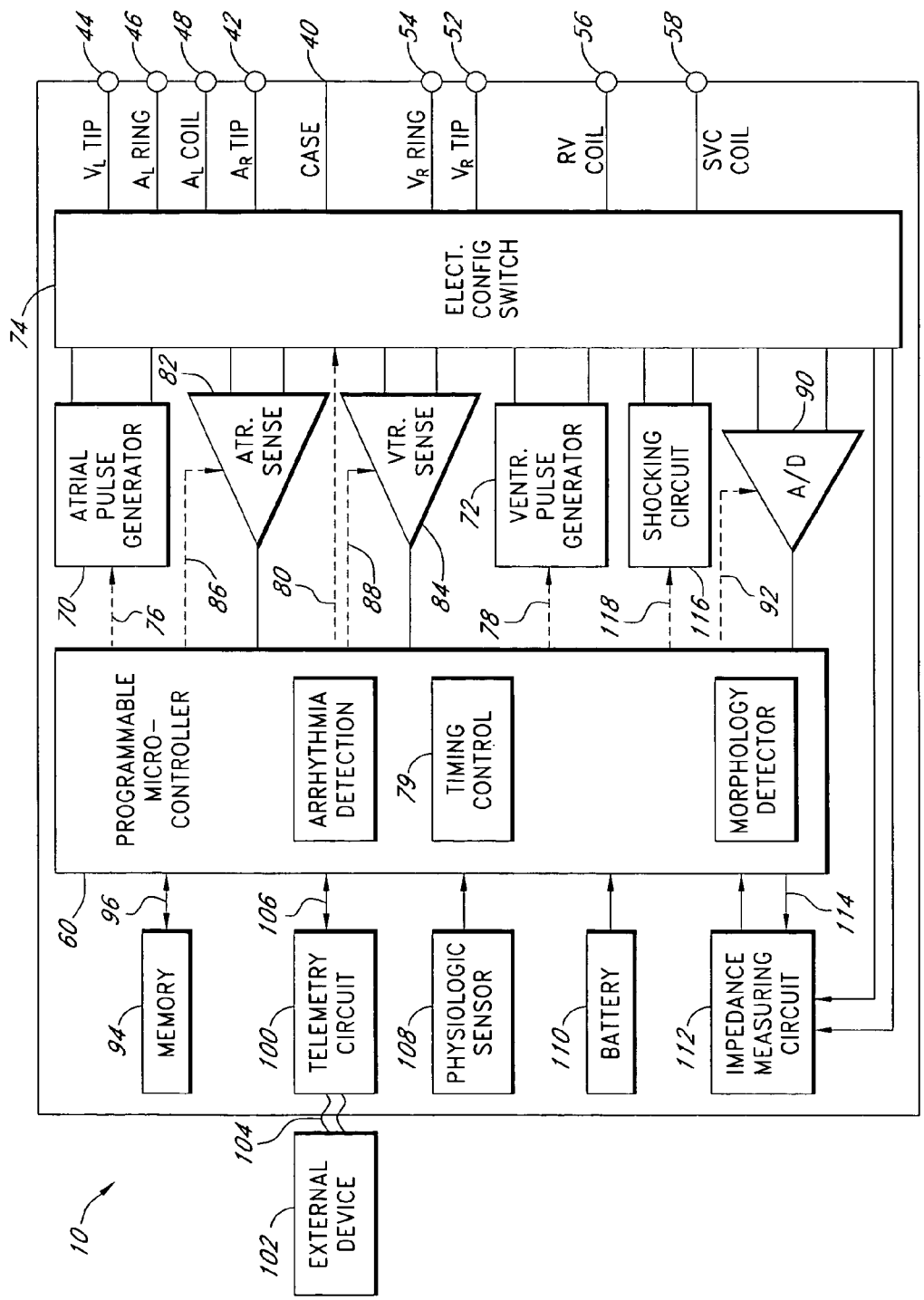
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to these embodiments. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators 70 and 72 may include dedicated, independent pulse generators, multiplexed pulse generators, or shared pulse generators. The pulse generators 70 and 72 are controlled by the microcontroller 60 via appropriate control signals 76 and 78 respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit 82 and 84 preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits 82 and 84 are connected to the microcontroller 60 which, in turn, is able to trigger or inhibit the atrial and ventricular pulse generators 70 and 72 respectively, in a demand fashion in response to the absence or presence of cardiac activity in the appropriate chambers of the heart.

For arrhythmia detection, the device 10 utilizes the atrial and ventricular sensing circuits 82 and 84 to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102, which, in certain embodiments, comprises a programmer. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 may be activated from a standby condition in response to an indication from a radio frequency (RF) detector (not shown) that signals of a predetermined strength are being received. The telemetry circuit 100 can communicate with the microcontroller 60 via a communication link 104.

The telemetry circuit 100 also advantageously allows intracardiac electrograms and status information relating to the operation of the device 10 (as contained in the microcontroller 60 or memory 94) to be sent to the external device 102 through an established communication link 104 as well as data from sensors 108. In certain embodiments, data from the sensors 108 is selectively sent continuously via the communication link 104 and, in alternative embodiments, the data from the sensors 108 is sent in frames and/or as a derived signal, e.g. an average or rate.

The device 10 comprises one or more physiologic sensors 108, commonly referred to as a "rate-responsive" sensor, because they are typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses.

While shown in FIG. 2 as being included internal to the stimulation device 10, it is to be understood that the sensors 108 may also be positioned outside and in communication with the stimulation device 10 and may include a variety of sensors 108 some or all of which may be external to the device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, ventricular gradient, etc. It is also to be understood, that in certain embodiments, the sensors 108 are capable of sensing multiple parameters and providing all the sensed parameters or a selected number of the parameters to the device 10.

Figure 3:
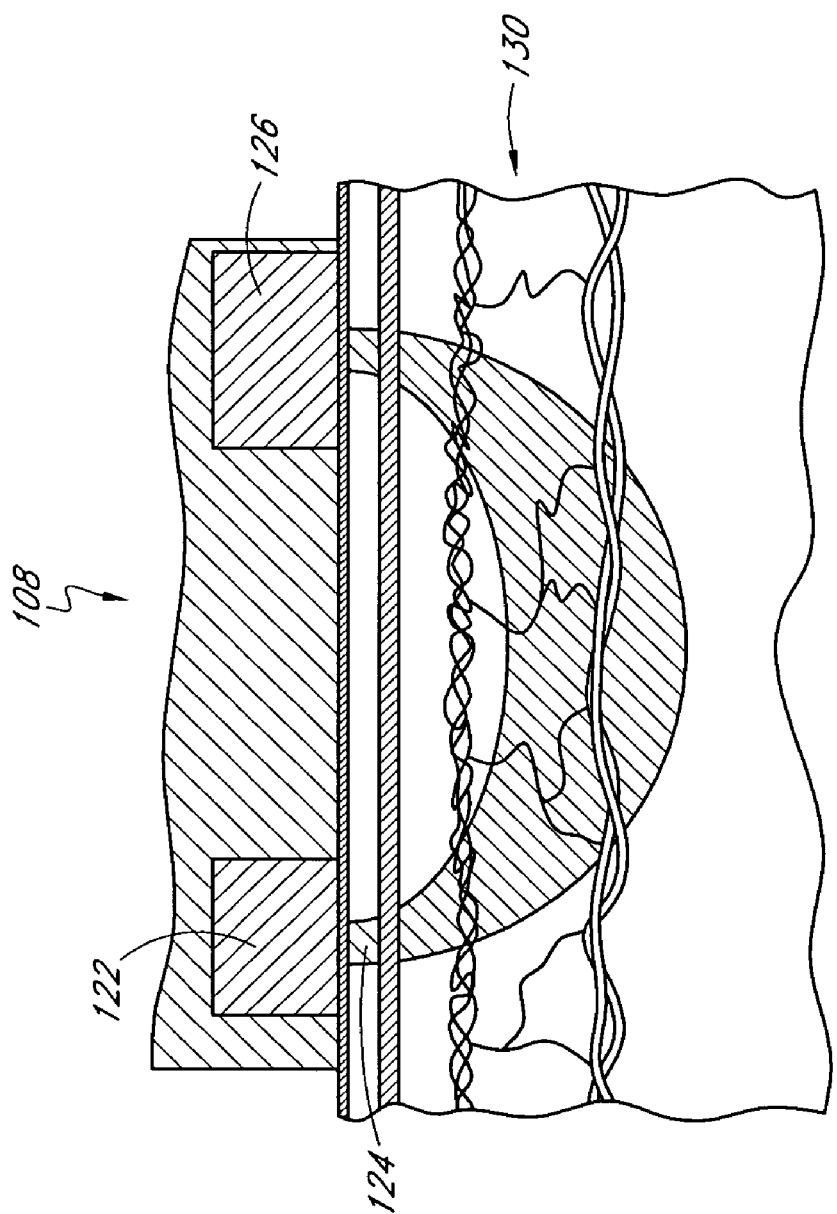
FIG. 3 illustrates the basic structure of an implantable photoplethysmography sensor.

In one embodiment, the sensors 108 comprise a first and a second physiologic sensors 108. In one embodiment, the first physiologic sensor 108 comprises a photoplethysmography (PPG) sensor which provides signals indicative of the volumetric and pressure changes of the patient's blood flow (FIG. 3). This PPG sensor 108 comprises a light emitter 122 which emits light 124 into the patient's tissue 130 and a light sensor 126 which receives the light 124 emitted by the light emitter 122 after having passed through the patient's tissue 130. In this embodiment, the PPG sensor 108 is arranged as a reflectance type sensor in that the light 124 incident on the light sensor 126 is reflected from the patient's tissue 130 after emission from the light emitter 122. In other embodiments, the PPG sensor is arranged as a transmittance type sensor wherein the light sensor 126 is arranged to directly receive light 124 from the light emitter 122 after having passed through the patient's tissue 130 which is interposed between the emitter 122 and sensor 126. Optical characteristics of tissue 130 vary with the quantity and characteristics of blood contained therein and thus the PPG sensor 108 can quantitatively sense the ebb and flow of the patient's blood to track hemodynamic output.

The light emitter 122, in this embodiment, comprises an IR LED emitting substantially non-visible IR range electromagnetic radiation into the patient's tissue 130. The light sensor 126 receives this emitted IR radiation and senses variations in the reflected light 124 to sense volumetric and pressure fluctuations in the amount and constitution of blood reflecting the light 124. The PPG sensor 108 can thus sense changes over time of the quantity and characteristics of blood flowing adjacent the PPG sensor 108. The PPG sensor 108 is commercially available and is well understood in the art, however additional details and embodiments of employing a PPG sensor 108 are found in the commonly assigned U.S. Pat. No. 6,575,912 to Robert Turcott which is incorporated herein in its entirety by reference.

The second physiologic sensor 108 comprises, in this embodiment, the aforementioned activity sensor. The second sensor 108 senses mechanical accelerations of the patient as an indicator of the intensity of physical activity in which they are currently engaged. The activity sensor 108 is typically employed to provide information indicative of the patient's metabolic need as an input to determine appropriate delivery of therapy by the device 10. In this embodiment, the second sensor 108 is also employed as an independent sensing source which is utilized to verify the reliability of the first physiological sensor 108. As previously mentioned, strenuous physical activity or other mechanical perturbations to the patient can cause disturbances in the sensing of the PPG sensor 108. The additional information provided by the second activity sensor 108 is used to correlate the output of the PPG sensor 108 to determine measures of the relative reliability of the signals being provided by each of the sensors 108 as well as the cardiac activity sensed by the indwelling leads as relates to the true physiological condition of the patient in a manner that will be described in greater detail below.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to these embodiments and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 4:
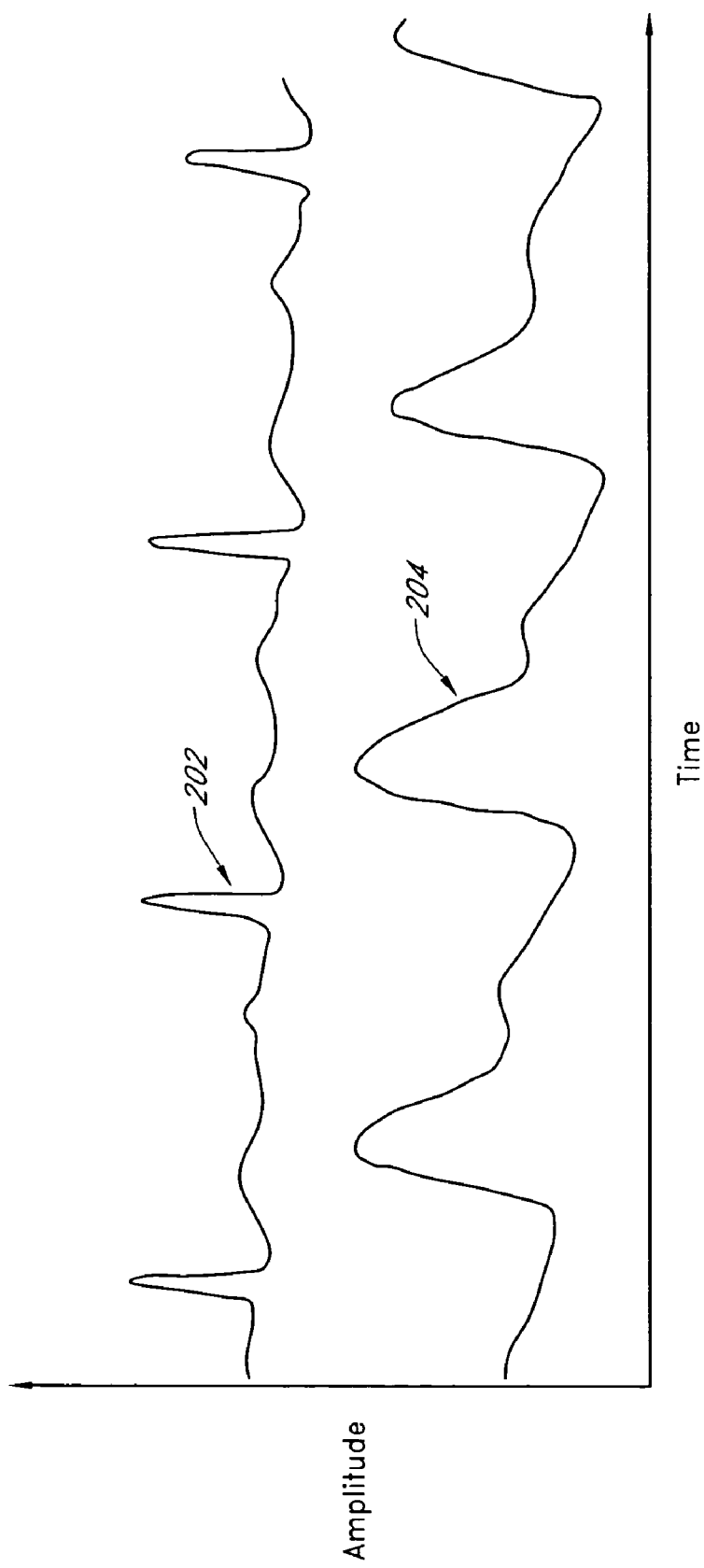
FIG. 4 is a waveform portraying a first time based patient signal, such as an IEGM, and a second time based signal, such as a photoplethysmography signal.

FIG. 4 illustrates a waveform of, in this embodiment, two separate independent sensor signals corresponding to a first patient signal 202 comprising, in this embodiment, an intracardiac electrogram (IEGM) and a second patient signal 204 comprising, in this exemplary embodiment, an optically based photoplethysmography (PPG) signal. The first patient signal 202 provides a signal indicative of the cyclical depolarization/repolarization of the patient's cardiac tissue and the second patient signal 204 provides a measure indicative of the volumetric fluctuations of the blood flow arising from the patient's cardiac activity. The first 202 and second 204 signals are independently sensed but are both directly or indirectly related to the patient's hemodynamic output. The second patient signal 204 directly measures the hemodynamic output and thus can provide an indication of hemodynamic compromise, however is subject to activity and physical shock disruptions which negatively affect the reliability of the second patient signal 204 as a true indicator of hemodynamic output. Thus, one embodiment is to correlate multiple patient signals, such as the first 202 and second 204 patient signals to attempt to establish a measure of the reliability of each of the multiple signals to increase accuracy of detection of hemodynamic insufficiency.

An examination of the waveforms corresponding to the first 202 and second 204 patient signals reveals that the respective waveforms are quite different in nature. In particular, the morphologies of the respective waveforms for the first 202 and second 204 patient signals are quite different. The first patient signal 202 corresponding, in this embodiment to an IEGM signal, exhibits the characteristic relatively sharp peaks (R-waves) of the PQRST waveform separated by relatively long periods of lower signal level. The second patient signal 204 corresponding to, in this embodiment, a PPG sensor providing the signals indicative of the volumetric and pressure fluctuations of the patient's blood flow, exhibits an initial relatively broad peak corresponding to the initial pressure rise and volumetric flow arising from the ventricular contraction followed by a relatively slower tail off with an interposed leveling off or slight subsequent increase in pressure and volumetric flow corresponding to the elastic nature of the circulatory tissue.

While the first 202 and second 204 patient signals both describe periodic major peaks occurring at substantially the same base frequency, these peaks are of different morphology and are also phase shifted with respect to each other. This phase shift arises principally from the time delay between the respective cardiac events indicated by the first patient signal 202 measured at a first location within the patient's body which induce a corresponding physical volumetric and pressure variation which propagates to and is measured at a second patient location displaced by some distance from the first patient location. Thus, the relative phase shift from the first 202 and second 204 patient signals can vary with the distance between the sensors providing these two signals and as a relatively fixed, discrete time is required for the physical propagation of the pumped blood fluid measured by the second patient signal 204, the phase difference between the first 202 and second 204 patient signals can vary with frequency (heart rate).

Thus the difficulty in obtaining useful information with respect to correlating these signals via a straight forward point by point comparison over time between the first 202 and second 204 patient signals is apparent. It will also be appreciated that a correlation of these signals as performed by the device 10 must operate within the operating constraints of the battery 110 and the microcontroller 60. The microcontroller 60 has a limited amount of available processing capacity while continuing to perform the previously described operations of sensing and determining and delivering therapy. Further, the battery 110 is of limited capacity as to limit the utilization of additional and/or higher power microcontrollers 60 which could contribute to an undesirable early consumption of the battery 110 which would indicate early replacement of the battery 110 which requires a follow-up invasive procedure on the patient. Thus, certain known dedicated signal processing algorithms and processors which may be suitable in other applications are less suitable for use in an implantable device 10 powered by the battery 110.

Figure 5:
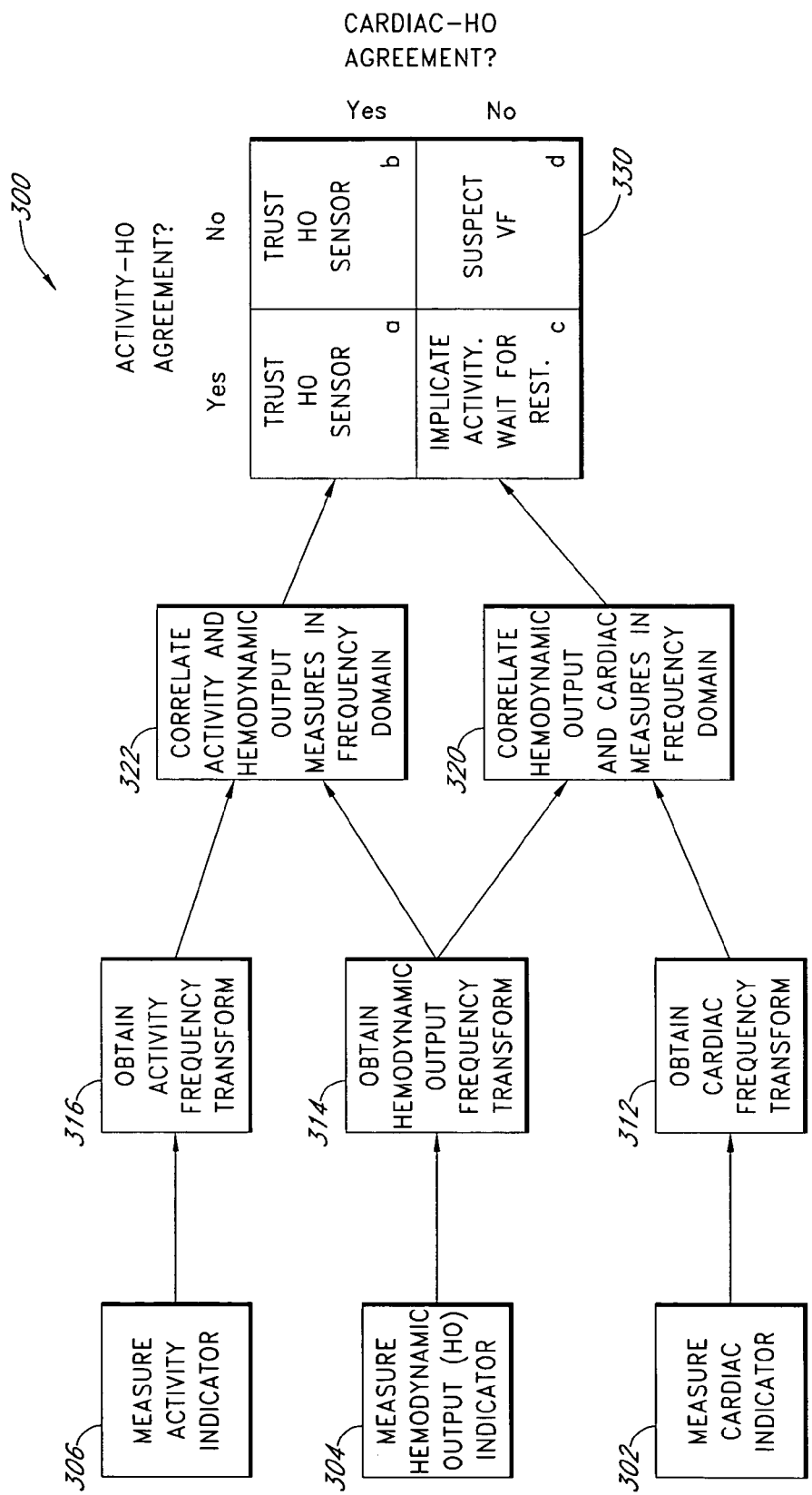
FIG. 5 is a flow chart of a method and system for correlating multiple patient sensor signals via the implantable device.

Embodiments thus include a system and methods for analyzing these multiple patient signals 202, 204 and correlating them to establish measures of their reliability as accurate indicators of the respective physiological conditions which they measure. FIG. 5 is a flow chart illustrating embodiments of such a method 300. The method first involves measurement steps wherein a plurality of physiological conditions of the patient is measured. In this embodiment, a first patient condition is measured in state 302 and in this embodiment this includes electrical sensing of the patient's cardiac activity resulting in the first patient signal 202. In state 304 a second patient parameter is measured, in this embodiment, comprising measurement of the patient's hemodynamic output (HO) resulting in the second patient signal 204. This embodiment also includes in state 306 measurement of a third patient parameter, in this embodiment a measure of patient activity, such as via an accelerometer.

To avoid the difficulties previously described with correlating multiple independent signals having different morphologies and a phase difference that is variable, this embodiment includes the aspect of analyzing these multiple signals in the frequency domain rather than in the time domain. This embodiment includes the general idea of transforming time based signals into corresponding signals in the frequency domain and examining the frequency spectra of the signals to determine their degree of correlation. Thus, in this embodiment, from each of the measurement states 302, 304, and 306 follow respective transformation states 312, 314, 316 wherein the respective time based signals are transformed into corresponding signals in the frequency domain.

In one more specific embodiment, the analysis of the multiple signals is performed by the implantable device 10 and microcontroller 60 and thus the measurement of periodic signals of the measurement states 302, 304, and 306 is performed at discreet intervals. Thus, this embodiment employs a discreet Fourier transform (DFT) and in particular a variation thereof, the fast Fourier transform (FFT). The FFT is particularly advantageous for this application in that the algorithm can efficiently obtain a frequency transformation of a time based signal in a particularly efficient algorithm for machine based calculations and thus can operate within the constraints of the limited capability of the microcontroller 60 and battery 110 of the implantable device 10.

The DFT and FFT effectively transform the time based signals into corresponding superimposed compositions of a plurality of sinusoids having different frequencies and amplitudes such that the summation of the plurality of sinusoids at their respective amplitudes sums to an approximation in the frequency domain of the time based signal. In each of the transformation states 312, 314, 316, the respective time based signal is considered as an N point time domain signal. This is transformed into two, N/2+1 point frequency domain signals comprising a real portion and an imaginary portion holding the amplitudes of the cosine and sine waves respectively. Thus, the N point time domain signal is decomposed into a frequency domain spectra having N frequency spectra. In one particular embodiment, a typical sampling period would be approximately 4 seconds with a sampling rate of approximately 100 Hz for an N=4096. The particular details of implementing an FFT with time based signals in a machined based process will be readily understood by one of ordinary skill in the art and the particular algorithms that may be employed in such a process will not be described in greater detail here.

For purposes of illustration, a high level description of this embodiment will now be described with the notation c(t) indicating the first patient signal 202 corresponding to an IEGM in the time domain and C(f) indicating the corresponding first patient signal in the frequency domain. Similarly, h(t) indicates the second patient signal 204 of hemodynamic output in the time domain and H(f) indicates the corresponding second patient signal 204 in the frequency domain. Likewise, in certain embodiments, a(t) indicates a third patient signal corresponding to activity such as measured by an accelerometer and A(f) indicates a corresponding transform of the activity signal into the frequency domain. It will be understood that while the notation used for explanation is for that of a continuous signal, as implemented in an electronic device, the exact implementation will be of a discreet digital approximation thereof.

A description will now follow of one embodiment of correlating multiple independent patient signals in the frequency domain. This embodiment is based on the coherence function which defines a scalar value ranging between zero and one characterizing the relationship between two signals. The relationship is based on the auto-power spectrum and cross-power spectrum of the signals as defined below.

The auto-power spectrum is defined as $$G_{XX} = X(f) \cdot X^*(f)$$

where $G_{XX}$=Auto-power spectrum for signal X
f=Frequency
X(f)=FFT of signal X
X*(f)=Complex conjugate of X(f).

An equation for the auto-power spectrum of the signal Y, can be similarly defined as equation 1 by simply replacing X with Y.

The cross-power spectrum is a type of complex relationship between two frequency signals and is defined similarly to the auto-power spectrum.

$$G_{YX} = Y(f) \cdot X^*(f)$$

where $G_{YX}$=Cross-power spectrum between signal X and signal Y
Y(f)=FFT of signal, Y.

Coherence is defined as the ratio of the cross-power spectrum to the auto-power spectra of both the signals:

$$\gamma^2 = \frac{|G_{YX}(f)|^2}{G_{XX}(f) \cdot G_{YY}(f)}$$

where

γ=Coherence [0,1].

Thus the coherence gives a readily calculated simple scalar value that can be used as an indicator of the degree of correlation between two independent signals. By transforming the multiple time based signals into the frequency domain, the common frequency characteristics of the respective signals are readily captured from the time domain and variable phase difference between the two signals which complicates analysis of the signals in the time domain does not complicate the analysis in the frequency domain. Likewise, the common periodic nature of the time based signals becomes readily apparent when considered in the frequency domain giving a relatively large coherence γ. Thus a relatively high value of the coherence function indicates that the respective signals share a strong periodic similarity in the time domain irrespective of differing signal morphologies and phase differences. A relatively large coherence value, in this embodiment, exceeding a threshold value, is used as a determinant that the multiple signals of interest are correlated and are providing reliable indicators of the patient's condition for use in determinations of therapy delivery.

Thus, from the transformation of states 312 and 314 follows a correlation calculation in state 320 comprising in this embodiment $$\gamma_{HC}^2 = \frac{|G_{HC}(f)|^2}{G_{CC}(f) \cdot G_{HH}(f)}.$$

And likewise following from the transformation of states 314 and 316 follows a correlation calculation of state 322 comprising in this embodiment $$\gamma_{AH}^2 = \frac{|G_{AH}(f)|^2}{G_{HH}(f) \cdot G_{AA}(f)}.$$

From these correlation calculations of states 320, 322 follows an evaluation state indicated by 330 in FIG. 5 indicating possible combinations of relative agreement as determined by the correlation calculations of states 320, 322 with regard to the relative agreement of the multiple patient signals measured in states 302, 304, and 306. In particular, the truth table indicated by 330 in FIG. 5 categorizes respective agreement between the activity indicator measured in state 306 and the hemodynamic output (HO) measured in state 304 and the agreement between the cardiac indicator measured in state 302 and the hemodynamic output indicator of 304. Thus the table indicates the various possibilities of relative agreement or disparity between the indications of these multiple signals corresponding to various aspects of the patient's condition. If agreement is indicated both between the activity and HO indicators as well as between the cardiac and HO indicators as indicated at 330A, a determination is made that the hemodynamic output indicator is providing a reliable indication of the patient's physiological condition and can be reliably used as an indicator for evaluation of the patient's condition.

Similarly as indicated by 330B, if the cardiac and hemodynamic output indicators are in agreement but the activity and hemodynamic indicators are not in agreement, a decision is still made that the hemodynamic output indicator is providing a reliable indication of the patient's hemodynamic output. If agreement is indicated between the activity and hemodynamic output indicators, however disagreement is indicated between the cardiac and hemodynamic output indicators, a conclusion is reached that patient activity or other physical perturbations are causing the disagreement. A decision is then made to discount the signal from the hemodynamic output indicator and to delay for some period of time to wait for return of reliable sensor operation, e.g. return of coherence between the cardiac and hemodynamic output indicators. Finally, as indicated in 330D, if no agreement is determined between either of the activity and the hemodynamic output indicators or the cardiac and hemodynamic output indicators, a decision is made that a ventricular fibrillation is likely accounting for the disagreement and the device 10 initiates delivery of appropriate shocking therapy in accordance with the programming of the implantable device 10.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. An implantable cardiac stimulation device comprising:
at least one lead adapted to be implanted in a patient so as to be able to deliver therapeutic stimulation to the heart of the patient;
a first sensor adapted to be implanted in the patient so as to sense a first signal indicative of electrophysiologic cardiac activity;
a second sensor adapted to be implanted in the patient so as to provide a second signal indicative of hemodynamic output;
a third sensor adapted to be implanted in the patient so as to provide a third signal indicative of patient activity; and
a controller that receives the signals from the first, second and third sensors, wherein the controller performs a frequency domain evaluation of the signals to determine whether the second signal is frequency related to the first signal and whether the second signal is frequency related to the third signal, and upon determining:
that the second signal is frequency related to the first signal, and the second signal is frequency related to the third signal, determines that the second signal is providing a reliable indication of the patient's physiological condition; and
that the second signal is frequency related to the first signal, and the second signal is not frequency related to the third signal, determines that the second signal is providing a reliable indication of the patient's physiological condition.

2. The device of claim 1, wherein, upon a determination that correlation is lacking between the first and second and the second and third signals, the controller determines a possible ventricular tachycardia condition.

3. The device of claim 1, wherein, upon a determination that correlation is lacking between the first and second, but does exist between the second and third signals, the controller determines that the lack of correlation between the first and second signals is due to an elevated activity level and inhibits delivery of therapy for a period of time.

4. The device of 1, wherein the controller correlates the signals in the frequency domain by transforming the signals from a time domain into the frequency domain and evaluating the degree to which they share frequency components.

5. The device of claim 4, wherein the controller performs a Fourier transform to transform the first and second signals into the frequency domain.

6. The device of claim 4, wherein the controller correlates the first and second signals by performing a coherence calculation of the transformed first and second signals.

7. The device of claim 1, wherein the first sensed signals correspond to sensed cardiac activity.

8. The device of claim 1, wherein the at least one physiological sensor comprises a plethysmography sensor.

* * * * *

UNITED STATES PATENT AND TRADEMARK OFFICE
CERTIFICATE OF CORRECTION

PATENT NO. : 7,596,412 B1 Page 1 of 1
APPLICATION NO. : 10/927971
DATED : September 29, 2009
INVENTOR(S) : Mark W. Kroll It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1120 days.

Signed and Sealed this

Twenty-eighth Day of September, 2010

David J. Kappos
*Director of the United States Patent and Trademark Office*